United States Patent [19]

Koerner et al.

[11] 4,281,147
[45] Jul. 28, 1981

[54] PROCESS FOR THE PRODUCTION OF AQUEOUS SOLUTIONS OF ALKALI ORGANOSILICONATES

[75] Inventors: Götz Koerner; Vaclav Kropac; Harald Rau, all of Essen, Fed. Rep. of Germany

[73] Assignee: Th. Goldschmidt AG, Essen, Fed. Rep. of Germany

[21] Appl. No.: 126,389

[22] Filed: Mar. 3, 1980

[30] Foreign Application Priority Data

Mar. 5, 1979 [GB] United Kingdom ................ 7664/79

[51] Int. Cl.³ .......................... C07F 7/04; C07F 7/08
[52] U.S. Cl. .................................. 556/459; 556/463
[58] Field of Search ............................... 556/459, 463

[56] References Cited

U.S. PATENT DOCUMENTS

| | | | |
|---|---|---|---|
| 2,438,055 | 3/1948 | Hyde et al. | 556/459 |
| 2,567,110 | 9/1951 | Hyde | 556/459 X |
| 2,574,265 | 11/1951 | Hyde | 556/459 X |
| 2,587,636 | 3/1952 | MacMullen | 556/459 |
| 2,729,572 | 1/1956 | Torkelson | 556/459 X |

OTHER PUBLICATIONS

Nou, "Chemistry and Technology of Silicones," Academic Press, N.Y. (1968), p. 86.

*Primary Examiner*—Paul F. Shaver

[57] ABSTRACT

A process for the preparation of aqueous solutions of alkali organosiliconates in which organoalkoxypolysiloxanes of the formula

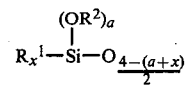

in which
R¹ is an alkyl residue with 1 to 3 carbon atoms, a vinyl residue and/or a phenyl residue,
R² is an alkyl residue with 1 to 4 carbon atoms,
a is a number ≦2, and
x is 1 to 1.25, are reacted with aqueous solutions of sodium hydroxide or potassium hydroxide having a concentration of 0.7 to 0.9 mole/100 g at temperatures ≧80° C. The liberated alcohol R²OH may be distilled and/or the concentration adjusted to the desired value by the addition of water. With the present invention, alkali chloride-free alkali organosiliconate solutions having high concentration can be obtained while avoiding a filtration step.

8 Claims, No Drawings

PROCESS FOR THE PRODUCTION OF AQUEOUS SOLUTIONS OF ALKALI ORGANOSILICONATES

BACKGROUND OF THE INVENTION

1. Field of the Invention

The invention relates to a process for the production of aqueous solutions of alkali organosiliconates and particularly, those whose organic residue is an alkyl residue with 1 to 3 carbon atoms, a vinyl residue and/or a phenyl residue, and whose alkali residue is a sodium or potassium ion.

2. Description of the Prior Art

Alkali methylsiliconate solutions are usually prepared by hydrolyzing methyltrichlorosilane and dissolving the methylsilicic acid formed in an alkaline solution. In this process, it is necessary to filter off the methylsilicic acid and to wash it carefully in order to remove the hydrochloric acid, which adheres to or is enclosed by the precipitate as completely as possible.

The filtration and washing of the methylsilicic acid create considerable difficulties because the precipitate is very voluminous and thus difficult to filter. Moreover, it occludes considerable amounts of hydrochloric acid within its bulk and some of this acid is inaccessible to the washing process.

In the subsequent reaction with alkali solution, the desired alkali methylsiliconates as well as alkali chlorides are formed, the latter being produced in an amount corresponding to the amount of occluded hydrochloric acid. Because the precipitated monomethylsilicic acid also occludes considerable quantities of water, it is necessary to concentrate the alkali siliconate solutions by distillation if higher concentrations are required.

A further, particularly serious disadvantage of this process is the fact that methylsilicic acid is not stable and condenses to form higher molecular weight products on storage. These materials are either insoluble or only slightly soluble in aqueous solutions of alkali hydroxide.

German Pat. No. 11 76 137 disclosed a process for the preparation of alkali methylsiliconates or their aqueous solutions in which the siliconates are obtained with significantly decreased amounts of contaminating alkali chloride. The process is characterized by the fact that the methylsilicic acid is precipitated from the alkali chloride-containing alkali methylsiliconate solutions by the addition of acid or of acid-releasing compounds until a pH of about 4 is reached below 60° C. Additionally, the separated methylsilicic acid is dissolved in an equimolar amount of alkali solution and, if necessary, the solution is freed from water.

However, the problems arising from the instability of the precipitated methylsilicic acid on storage and the consequence that it must be processed at once, still exist with the process of German Pat. No. 11 76 137. Moreover, according to column 4, lines 6 ff. of this patent, the methylsilicic acid, precipitated according to this process, also contains considerable quantities of water. Thus, even if only a 30% solution is to be prepared from the solution of sodium methylsiliconate which has been formed, water must be removed by distillation.

SUMMARY OF THE INVENTION

We have discovered a method for producing alkali chloride free organosiliconate solutions. Using this process, a filtration step can be completely or almost completely avoided and solutions of any concentration can be prepared.

More particularly, the process of the present invention comprises reacting organoalkoxypolysiloxanes of the general formula

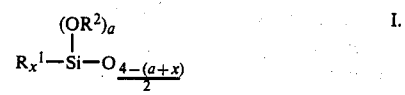

in which
R$^1$ is an alkyl residue with 1 to 3 carbon atoms, a vinyl residue and/or a phenyl residue,
R$^2$ is an alkyl residue with 1 to 4 carbon atoms,
a is a number $\leq 2$ and
x is 1 to 1.25, with aqueous solutions of sodium hydroxide or potassium hydroxide having a concentration of 0.07 to 0.9 moles/100 g at temperatures $\geq 80°$ C., if necessary, distilling off the released alcohol, R$^2$OH, and/or adjusting the concentration of the solution of the reaction product with water to the desired value.

DESCRIPTION OF THE PREFERRED EMBODIMENT

Preferably, R$^1$ is a methyl residue, and R$^2$ is an ethyl residue, a has a value of 0.1 to 0.8, and x a value of 1.0.

It is surprising that organoalkoxypolysiloxanes of Formula I, which have a relatively high molecular weight, that is, in which a $\leq 1$, can still be dissolved in an alkaline solution to form monomeric or slightly condensed alkali organosiliconates.

In the process of the present invention, it is important that alkaline solutions of a particular concentration range be used. If the concentration is below 0.7 moles/100 g, the organoalkoxypolysiloxanes do not dissolve and the formation of the desired siliconate does not take place. If a concentration of 0.9 moles/100 g is exceeded, the condensation reaction is favored and, instead of clear solutions of alkali organosiliconates, gelled products are obtained. The degree of gelling depends on the concentration of the caustic solution.

With the present process, solutions which contain 40 weight percent and more of alkali siliconate can be processed. The solutions can be adjusted to the desired concentration by dilution with water.

The alcohol R$^2$OH, which is released by the reaction may remain in or be distilled from the reaction mixture. Frequently, it is desirable to leave the alcohol in the aqueous alkali organosiliconate solution. Thus, in many applications, for example, when impregnating and saturating mineral raw materials with such solutions in order to hydrophobize them, an alcohol content improves the penetration by the solution.

The organoalkoxypolysiloxane starting product of Formula I can be produced in a manner known in the art by reacting appropriate chlorosilanes with water/alcohol mixtures. This starting product has the advantage of possessing a high storage stability. Accordingly, the inventive process starts with storage-stable products and, in the course of the process, the formation of unstable intermediates is avoided. Thus, by using the method of the present invention, alkali chloride-free alkali organosiliconate solutions of high concentration may be obtained in a simple and reproducible manner.

The following examples illustrate the present invention. All percentages in the examples are weight percentages.

EXAMPLE 1

A 1000 ml flask, equipped with stirrer and reflux condenser, is filled with 482.5 g of a 32.6% sodium hydroxide solution and heated to 110° C. From a dropping funnel, 263 g of a polymethylethoxysiloxane of formula

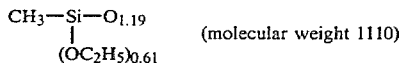

$$CH_3-Si-O_{1.19} \atop (OC_2H_5)_{0.61} \quad \text{(molecular weight 1110)}$$

are added dropwise with stirring at such a rate that the reflux remains constant. At the same time, the temperature drops to 85° C. The methylsiliconate solution is cooled to room temperature and adjusted to a solids content of 40% by the addition of 154.7 g of water. Yield: 360.1 g of siliconate (solid). In the analysis of the methylsiliconate solution 23.2% of $CH_3SiO_{1.5}$, 14.0% of $Na_2O$ and less than 0.001% of Cl were found.

EXAMPLE 2

The procedure described in Example 1 is repeated and 284.7 g of a polymethylethoxysiloxane of formula

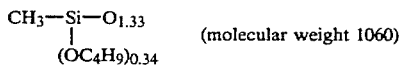

$$CH_3-Si-O_{1.33} \atop (OC_4H_9)_{0.34} \quad \text{(molecular weight 1060)}$$

are used. When the reaction is completed, the reaction mixture in the flask is diluted with 510 ml of water. Then, 80 g of n-butanol and 16 g of water are distilled off from the mixture. An approximately 30% solution of methylsiliconate with 335 g of solids is obtained.

EXAMPLE 3

The procedure described in Example 1 is repeated, except that 466 g of 47.2% potassium hydroxide solution is used instead of the sodium hydroxide solution. After the reaction, 729 g of a 52% solution of potassium methylsiliconate are obtained.

EXAMPLE 4

To the apparatus, described in Example 1, 306 g of a 46.1% aqueous potassium hydroxide solution are added and heated to 120° C. Subsequently, 300 g of the polyphenylmethoxysiloxane of formula

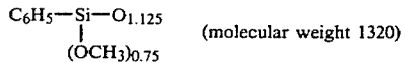

$$C_6H_5-Si-O_{1.125} \atop (OCH_3)_{0.75} \quad \text{(molecular weight 1320)}$$

are added dropwise. Initially, the polyphenylmethoxysiloxane dissolves without liberating methanol, this is formed only after the polysiloxane has dissolved. After reaction, the reaction solution is diluted with 150 g of water. A 58.4% solution of potassium phenylsiliconate, containing 655.8 g of solids, is obtained.

EXAMPLE 5

The procedure described in Example 1 is repeated, except that 270 g of a polymethylethoxysiloxane of formula

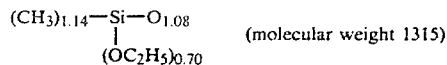

$$(CH_3)_{1.14}-Si-O_{1.08} \atop (OC_2H_5)_{0.70} \quad \text{(molecular weight 1315)}$$

are added dropwise to 462 g of a 32% sodium hydroxide solution at 80° C. to 110° C. A 42% sodium methylsiliconate solution is obtained, which contains 732 g of solids and less than 0.001% of chloride.

EXAMPLE 6

The apparatus, described in Example 1, is filled with 149.3 g of a 46% potassium hydroxide solution and heated to 110° C. Subsequently, 119.6 g of the polypropylisopropoxysiloxane of formula

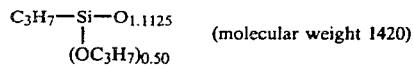

$$C_3H_7-Si-O_{1.1125} \atop (OC_3H_7)_{0.50} \quad \text{(molecular weight 1420)}$$

are added dropwise. A 56% solution of the chloride-free potassium propylsiliconate, containing 268.9 g of solids, is obtained.

EXAMPLE 7

The procedure described in Example 1 is repeated with the difference that 250 g of the polymethylethoxysiloxane of formula

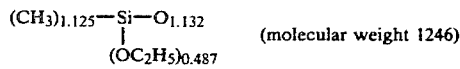

$$(CH_3)_{1.125}-Si-O_{1.132} \atop (OC_2H_5)_{0.487} \quad \text{(molecular weight 1246)}$$

are added dropwise to 444 g of a 32% sodium hydroxide solution at 80° C. to 110° C. A 44.5% solution of the chloride-free sodium polymethylsiliconate, containing 694 g of solids, is obtained.

What is claimed is:

1. In a process for the preparation of aqueous solutions of alkali organosiliconates which comprises reacting an organoalkoxypolysiloxane having the formula

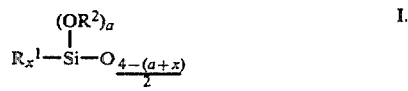

$$R_x^1-Si-O_{\frac{4-(a+x)}{2}} \atop (OR^2)_a \quad \text{I.}$$

wherein
$R^1$ is an alkyl residue with 1 to 3 carbon atoms, a vinyl residue and/or a phenyl residue,
$R^2$ is an alkyl residue with 1 to 4 carbon atoms,
a is a number $\leq 2$, and
x is 1 to 1.25,
with an aqueous solution of sodium hydroxide or potassium hydroxide having a concentration of 0.7 to 0.9 mole/100 g at temperatures $\geq 80°$ C.

2. The process of claim 1 wherein any alcohol liberated during the reaction is distilled from the reaction mixture.

3. The process of claim 1 wherein after the reaction, the concentration of the reaction mixture is adjusted with water to the desired value.

4. The process of claim 1, 2, or 3 wherein $R^1$ is methyl.

5. The process of claim 1, 2, or 3 wherein $R^2$ is ethyl.

6. The process of claim 1, 2, or 3 wherein a is from 0.1 to 0.8.

7. The process of claim 1, 2, or 3 wherein x is 1.

8. The process of claim 1, 2, or 3 wherein $R^1$ is methyl and $R^2$ is ethyl.

* * * * *